US012544516B2

(12) United States Patent
Berler et al.

(10) Patent No.: US 12,544,516 B2
(45) Date of Patent: Feb. 10, 2026

(54) ULTRA-LOW WASTE DISPOSABLE SYRINGE WITH SELF-ADJUSTING INTEGRATED SAFETY FEATURES

(71) Applicant: Sharps Technology, Inc., Melville, NY (US)

(72) Inventors: Barry B. Berler, Huntingdon Valley, PA (US); Alan Blackman, New York, NY (US)

(73) Assignee: Plasto Technology Group LLC, Huntingdon Valley, PA (US)

( * ) Notice: Subject to any disclaimer, the term of this patent is extended or adjusted under 35 U.S.C. 154(b) by 728 days.

(21) Appl. No.: 16/908,584

(22) Filed: Jun. 22, 2020

(65) Prior Publication Data

US 2020/0405974 A1 Dec. 31, 2020

Related U.S. Application Data

(60) Provisional application No. 62/867,811, filed on Jun. 27, 2019.

(51) Int. Cl.
*A61M 5/31* (2006.01)
*A61M 5/32* (2006.01)
*A61M 5/315* (2006.01)

(52) U.S. Cl.
CPC .......... *A61M 5/326* (2013.01); *A61M 5/3129* (2013.01); *A61M 2005/311* (2013.01); *A61M 2005/31516* (2013.01)

(58) Field of Classification Search
CPC ................ A61M 5/3234; A61M 5/322; A61M 2005/3235; A61M 2005/3241; A61M 2005/3239; A61M 2005/3265; A61M 2005/3131; A61M 2005/311; A61M 2005/323; A61M 2005/3231; A61M 2005/3236
See application file for complete search history.

(56) References Cited

U.S. PATENT DOCUMENTS

| | | | |
|---|---|---|---|
| 4,559,043 | A | 12/1985 | Whitehouse et al. |
| 5,104,384 | A | 4/1992 | Parry |
| 5,205,826 | A | 4/1993 | Chen |
| 5,306,258 | A | 4/1994 | de la Fuente |
| 5,314,503 | A | 5/1994 | Bobrove et al. |

(Continued)

FOREIGN PATENT DOCUMENTS

| | | |
|---|---|---|
| CA | 223649 | 7/2006 |
| CA | 2236049 | 7/2006 |

*Primary Examiner* — Emily L Schmidt

(74) *Attorney, Agent, or Firm* — LaMorte & Associates PC

(57) ABSTRACT

A system with a needle head that attaches to a syringe assembly. The syringe assembly contains a barrel and a plunger. The plunger has a bore opening that is accessible from within the barrel. A tubular spacer is disposed within the barrel. The tubular spacer defines a central opening. The needle head has a needle that extends from a needle base. The needle base extends into the central opening of the tubular spacer. A plug is provided that blocks access to the needle. The plug is displaced out of the central opening of the tubular spacer and into the opening in the plunger as the plunger contacts and displaces the tubular spacer in the barrel. As the plug is displaced from the tubular spacer, the plug transfers into the bore opening within the plunger. This enables the plunger to press flush against the tubular spacer.

12 Claims, 7 Drawing Sheets

(56) References Cited

U.S. PATENT DOCUMENTS

| | | | | |
|---|---|---|---|---|
| 5,370,628 | A | 12/1994 | Allison et al. | |
| 5,385,555 | A | 1/1995 | Hausser | |
| 5,460,611 | A | 10/1995 | Alexander | |
| 5,733,264 | A | 3/1998 | Flowers | |
| 5,891,092 | A | 4/1999 | Castellano | |
| 5,902,270 | A | 5/1999 | Jentzen | |
| 6,616,636 | B2 | 9/2003 | Lee | |
| 6,626,863 | B1 | 9/2003 | Berler | |
| 7,527,607 | B2 | 5/2009 | Botich | |
| 2003/0130623 | A1* | 7/2003 | Chen | A61M 5/3234 604/110 |
| 2007/0016140 | A1 | 1/2007 | Berler | |
| 2007/0016145 | A1 | 1/2007 | Berler | |
| 2007/0185447 | A1* | 8/2007 | Lu | A61M 5/3234 604/110 |
| 2008/0009808 | A1 | 1/2008 | Berler | |
| 2008/0097337 | A1 | 4/2008 | Judd et al. | |
| 2008/0319346 | A1 | 12/2008 | Crawford et al. | |
| 2010/0076378 | A1 | 3/2010 | Runfola | |
| 2011/0213304 | A1* | 9/2011 | Schraga | A61M 5/3234 604/110 |
| 2015/0374928 | A1* | 12/2015 | Hsu | A61M 5/3232 604/198 |
| 2016/0045676 | A1 | 2/2016 | Klippenstein | |
| 2016/0279333 | A1 | 9/2016 | Russo et al. | |
| 2016/0279344 | A1 | 9/2016 | Shluzas et al. | |
| 2016/0367764 | A1 | 12/2016 | Doyle | |
| 2017/0319791 | A1 | 11/2017 | Giambattista et al. | |

* cited by examiner

ULTRA-LOW WASTE DISPOSABLE SYRINGE WITH SELF-ADJUSTING INTEGRATED SAFETY FEATURES

RELATED APPLICATIONS

This application claims the benefit of U.S. provisional patent application No. 62/867,811, filed Jun. 27, 2019.

FIELD OF THE INVENTION

In general, the present invention relates to syringes that are used to make injections through a needle or cannula. More particularly, the present invention relates to multiple dose syringes that are designed to minimize the amount of injection material retained within the syringe after the syringe is used for the last dose.

PRIOR ART DESCRIPTION

Millions of injections are performed in the United States of America each year. The injections are typically performed using a hypodermic needle and a syringe. The length of the hypodermic needle and the gauge of the needle depend upon the application and whether the injection is intramuscular, subcutaneous, intravenous, or intradermal. The compounds being injected also vary widely. Some injection materials, such as saline, are very inexpensive. However, many pharmaceutical compounds, such as certain gene therapy compounds, can cost tens of thousands of dollars per injection. As such, a fraction of a milliliter of the pharmaceutical can be worth hundreds of dollars.

When a traditional hypodermic needle and syringe are used to perform an injection, there is inevitably some volume of injection material that remains within the needle and syringe after the injection is complete. The pharmaceutical material remaining is thrown away with the needle and syringe after the injection. This wasted pharmaceutical material adds up to billions of dollars in wasted pharmaceuticals, when all injections are considered.

In the prior art, thought is rarely given to the volume of residual material that inherently remains within a hypodermic syringe and needle. Some needle and syringe assemblies have been designed where a syringe plunger and a needle head make flush contact. Such prior art designs are exemplified by U.S. Pat. No. 6,616,636 to Lee and U.S. Pat. No. 5,902,270 to Jentzen. However, in a real healthcare environment, such as a hospital, different syringes are used with many different needle heads, depending upon the specific medical application. Some needle head and syringe combinations are efficient in the discharge of pharmaceutical compounds and some are not.

The problem becomes more complicated when a needle head and syringe are part of a safety syringe assembly. Safety syringe assemblies are designed to both perform an injection and to provide some mechanism for minimizing the likelihood of a needle stick injury. Needle stick injuries are commonplace among healthcare workers. Needle stick injuries are defined by the United States National Institute of Occupational Safety and Health as injuries caused by needles such as hypodermic needles, blood collection needles, intravenous (IV) stylets, and needles used to connect parts of IV delivery systems. Needle stick injuries can transfer blood-borne pathogens such as Hepatitis B virus, Hepatitis C virus, Human Immunodeficiency Virus (HIV) and Covid-19. For healthcare workers, needle stick injuries are responsible for a significant proportion of these diseases in the healthcare workforce.

It has been estimated by the Centers for Disease Control, that in the United States of America, more than three million healthcare workers are exposed to blood and bodily fluids via needle mishaps each year. Most healthcare workers are trained in procedures for using and disposing of used needles. For example, needles should not be recapped, in order to prevent the potential for needle stick injuries. However, many studies have revealed that recapping is still prevalent among healthcare workers.

In an attempt to reduce the number of needle stick injuries, various safety needles have been developed that act to automatically cover a needle the instant the needle is retracted from the skin. This is typically accomplished by advancing a tubular sheath along the shaft of the needle until the sheath covers the tip of the needle. Such prior art is exemplified by U.S. Pat. No. 6,626,863, U.S. Patent Application Publication No. 2007/0016140, U.S. Patent Application Publication No. 2007/0016145, and U.S. Patent Application Publication No. 2008/009808. However, integrating a safety mechanism within a needle head typically takes additional room within the needle head. More room in the needle head means that there is more dead space in the needle head where residual pharmaceutical compounds can collect. As a consequence, there are often opposing concerns that must be balanced in a design. The safety features of a design are balanced with the wasted pharmaceutical retained because of the safety features.

A need therefore exists for an improved hypodermic needle and syringe assembly where the needle is automatically shielded after an injection and wherein the assembly does not retain any significant volume of the material being injected. This need is met by the present invention as described and claimed below.

SUMMARY OF THE INVENTION

The present invention is a needle and syringe system, wherein a needle head is attached to a syringe assembly. The syringe assembly contains a barrel and a plunger. The plunger has a bore opening formed in one end that is accessible from within the barrel.

A tubular spacer is disposed within the barrel. The tubular spacer defines a central opening that extends through the tubular spacer.

The needle head selectively attaches to the syringe assembly. The needle head has a needle that extends from a needle base. The needle base extends into the central opening of the tubular spacer.

A plug is provided inside the barrel that blocks access to the needle by blocking the central opening of the tubular spacer. The plug is displaced out of the central opening of the tubular spacer and into the opening in the plunger as the plunger contacts and displaces the tubular spacer in the barrel. As the plug is displaced from the tubular spacer, the plug transfers into the bore opening within the plunger. This enables the plunger to press flush against the tubular spacer.

As the tubular spacer is displaced by the plunger, the tubular spacer moves a safety sheath that advances and covers the needle, therein rendering the needle safe.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

The present invention needle and syringe system can be configured in many ways and can be adapted for use in many applications. However, only one exemplary embodiment is selected for the purposes of description and illustration. The illustrated embodiment, however, is merely exemplary and should not be considered a limitation when interpreting the scope of the appended claims.

Figure 1:
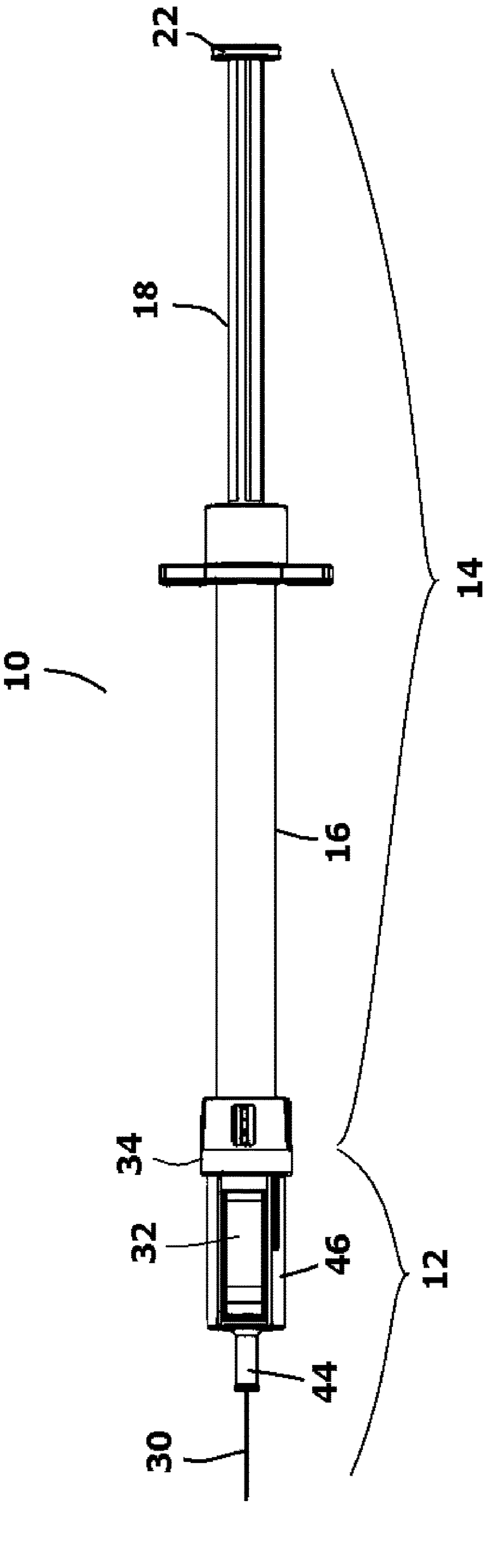
FIG. 1 shows the head of a needle and syringe system in a condition ready for use with its needle exposed.
Figure 2:
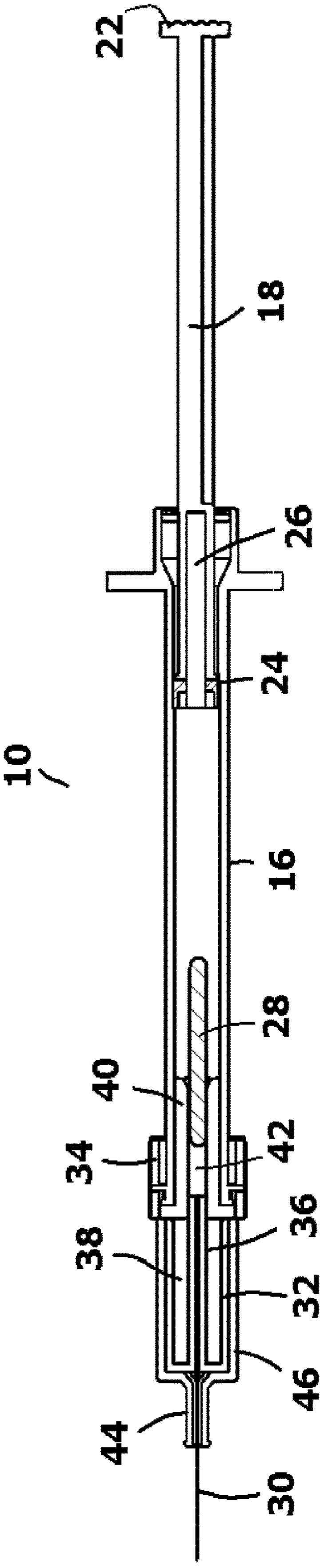
FIG. 2 is a cross-sectional view of the exemplary embodiment of FIG. 1.
Figure 3:
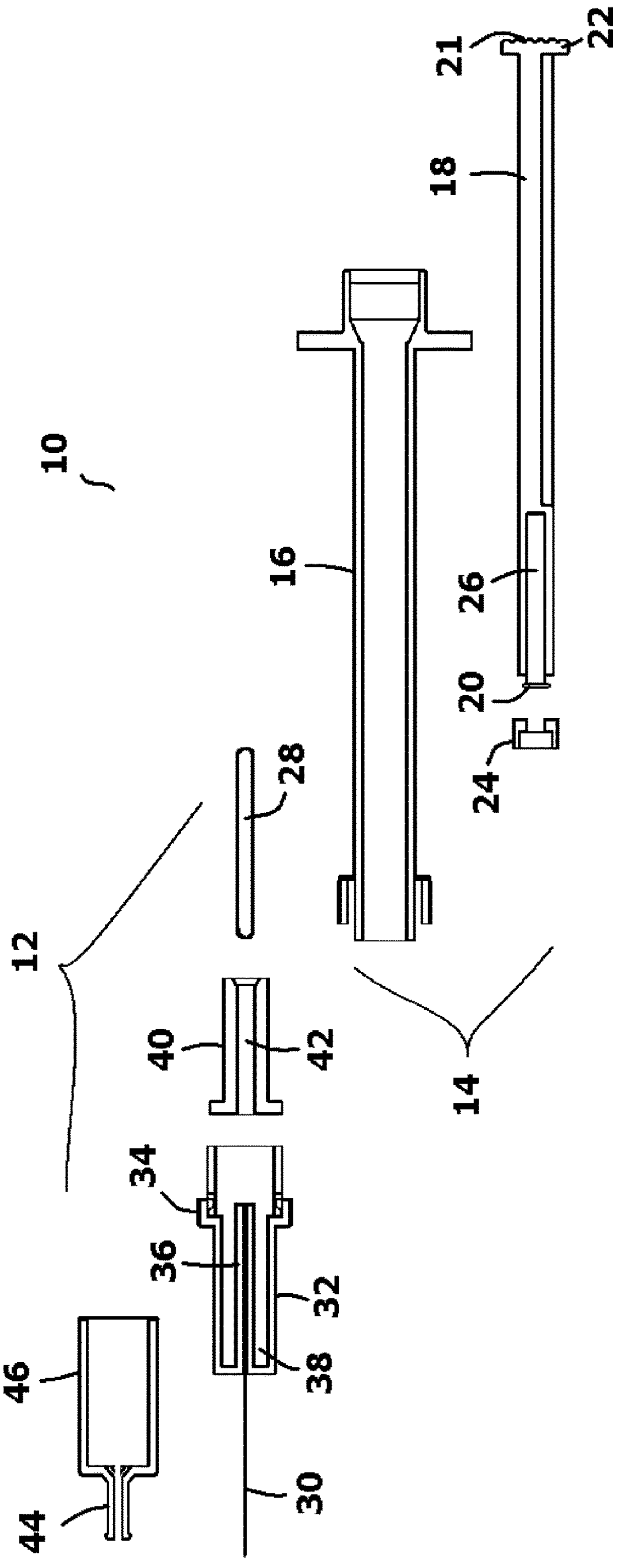
FIG. 3 is an exploded cross-sectional view of the exemplary embodiment of FIG. 1.

Referring to FIG. 1, FIG. 2, and FIG. 3, the present invention needle and syringe system 10 is shown. In the shown embodiment, the needle and syringe system 10 includes two primary subassemblies that are selectively joined by a healthcare professional prior to use. The primary subassemblies include a head subassembly 12 and a syringe subassembly 14. The head subassembly 12 mechanically engages the syringe subassembly 14 with a mechanical connection, as is later explained. Accordingly, different head subassemblies can be selectively attached to different syringe subassemblies according to the needs of the healthcare professional.

The syringe subassembly 14 includes a syringe barrel 16 and a plunger rod 18 that extends into the syringe barrel 16. The plunger rod 18 has a first end 20 and an opposite second end 21. The first end 20 extends into the syringe barrel 16. The second end 21 terminates with a thumb pad 22 that is used to manually move the plunger rod 18 in the syringe barrel 16 between a fully advanced first position and a fully retracted second position. The first end 20 of the plunger rod 18 is terminated with an elastomeric piston head 24. The piston head 24 is annular in shape and seals the plunger rod 18 with the interior of the syringe barrel 16.

A blind bore 26 is formed in the plunger rod 18, wherein the bling bore 26 is open at the first end 20 of the plunger rod 18. The annular shape of the piston head 24 prevents the piston head 24 from blocking access to the blind bore 26 from within the syringe barrel 16. The blind bore 26 extends for a first length into the plunger rod 18.

An elongated plug 28 is provided. The elongated plug 28 has the same length as the bore blind 26 in the plunger rod 18 and is capable of being fully received within the blind bore 26 of the plunger rod 18. Although the elongated plug 28 moves between the head subassembly 12 and the syringe subassembly 14, the elongated plug 28 is initially packaged as part of the head subassembly 12, as will later be explained. The head subassembly 12 holds a needle 30. The needle 30 extends forward from a plastic needle base 32. The needle base 32 contains a collar 34 that is sized and shaped to engage the syringe subassembly 14. The collar 34 engages the syringe barrel 16 with a mechanical connection, such as a threaded connection or a bayonet connection. This enables a healthcare professional to be able to manually connect and disconnect the head subassembly 12 and the syringe subassembly 14. A central post 36 is concentrically disposed within the collar 34. A cylindrical cavity 38 separates the collar 34 from the central post 36. The needle 30 extends into and through the central post 36. Since the needle 30 is attached to the central post 36, the central post 36 is attached to the collar 34, and the collar 34 is attached to the syringe barrel 16, there is no relative movement between the needle 30 and the syringe barrel 16 during the operation of the needle and syringe system 10.

A tubular spacer 40 is provided as part of the head subassembly 12. The tubular spacer 40 is positioned in the cylindrical cavity 38 between the central post 36 and the collar 34. The tubular spacer 40 defines a central conduit 42 that receives the central post 36 of the needle base 32. The length of the cylindrical cavity 38 in the tubular spacer 40 is exactly the same as the length of the central post 36. The tubular spacer 40 is separate from the needle base 32 and is free to slide along the length of the central post 36.

A safety sheath 44 is provided that surrounds part of the needle 30. The safety sheath 44 is attached to an actuator cap 46. The actuator cap 46 is sized to extend over the exterior of the needle base 32. The actuator cap 46 can reciprocally move along the exterior of the needle base 32. The actuator cap 46 can be selectively locked and unlocked using a mechanical release 48 that is accessible on the exterior of the syringe subassembly 14. It will therefore be understood that the actuator cap 46 can be selectively released and moved relative to the needle 30 and the needle base 32.

Figure 4:
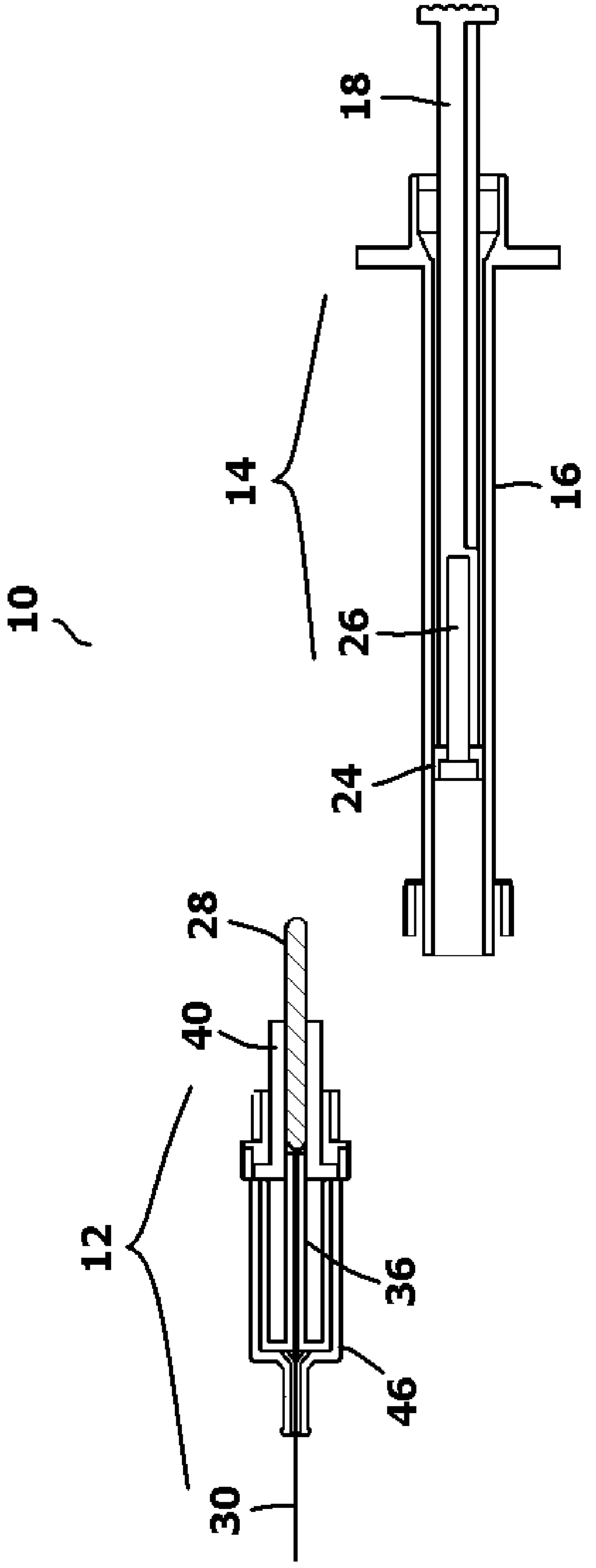
FIG. 4 is a cross-sectional view of a head subassembly prior to attachment with a syringe subassembly.

Referring to FIG. 4 in conjunction with FIG. 2 and FIG. 3, it can be seen that prior to use, the elongated plug 28 is part of the head subassembly 12. The elongated plug 28 is positioned within the central conduit 42 of the tubular spacer 40. This blocks the needle 30 and isolates the needle 30 within the head subassembly 12 as the head subassembly 12 and the syringe subassembly 14 are interconnected. Once the head subassembly 12 is attached to the syringe barrel 16, the loading of the needle and syringe system 10 can begin. To load the needle and syringe system 10, the plunger rod 18 is advanced into the syringe barrel 16. As the first end 20 of the plunger rod 18 moves toward the head subassembly 12, the first end 20 contacts the elongated plug 28. The elongated plug 28 enters the blind bore 26 in the plunger rod 18. The blind bore 26 receives and retains the elongated plug 28 with an interference fit.

Figure 5:
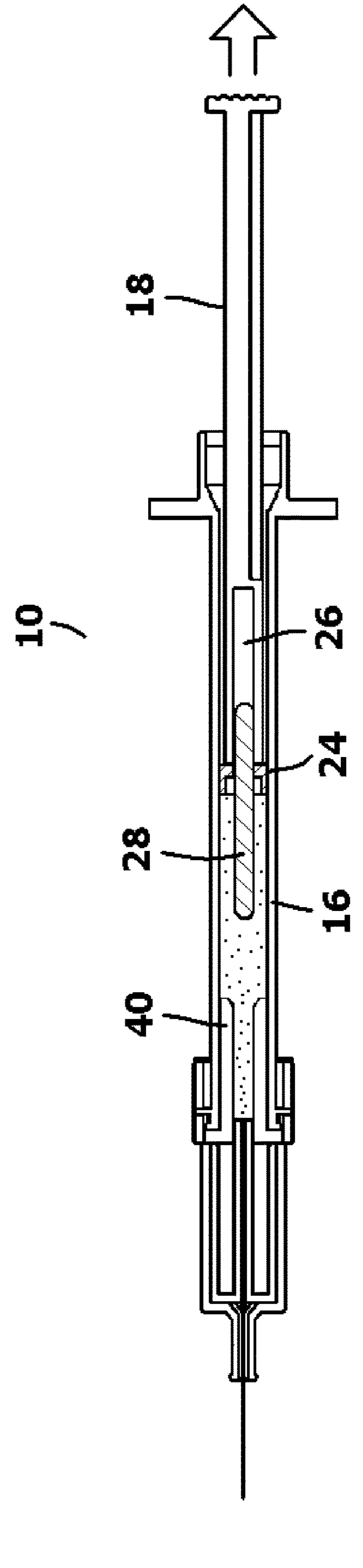
FIG. 5 is a cross-sectional view of the exemplary embodiment of FIG. 1 showing material being drawn into the needle and syringe system.

Referring to FIG. 5 in conjunction with FIG. 4, it can be seen that after the elongated plug 28 is received into the blind bore 26, the plunger rod 18 is retracted. The plunger rod 18 retains the elongated plug 28 and pulls the elongated plug 28 out of the tubular spacer 40. This clears the needle 30 and enables fluid to be drawn into the syringe barrel 16 through the needle 30.

Figure 6:
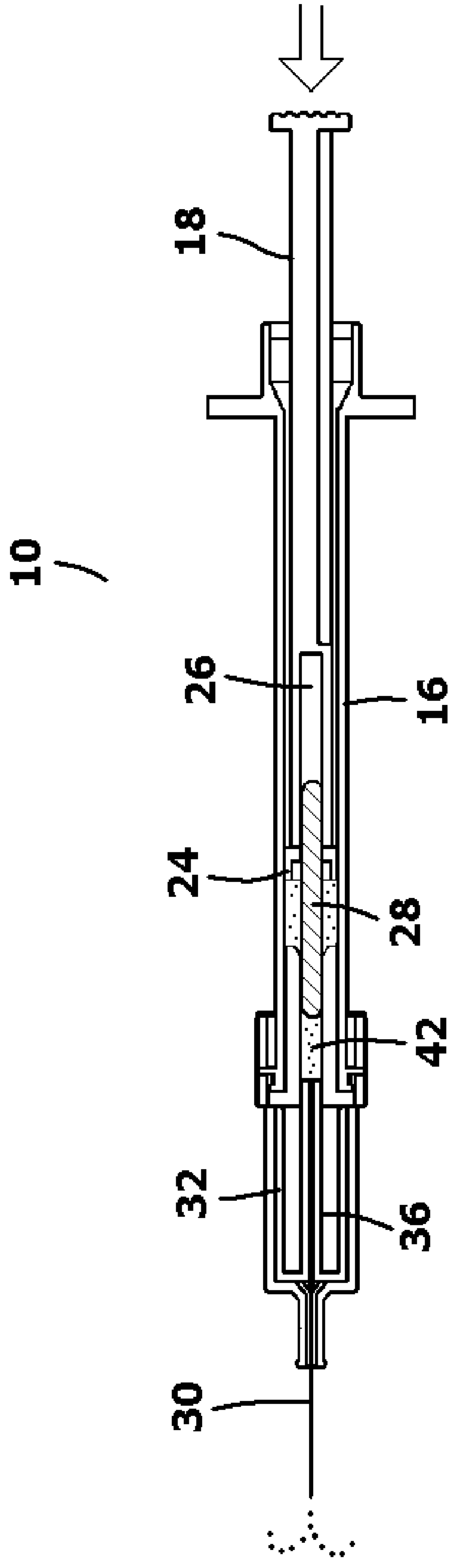
FIG. 6 shows a cross-section of the exemplary embodiment of FIG. 1 showing material being displaced from the needle and syringe system.
Figure 7:
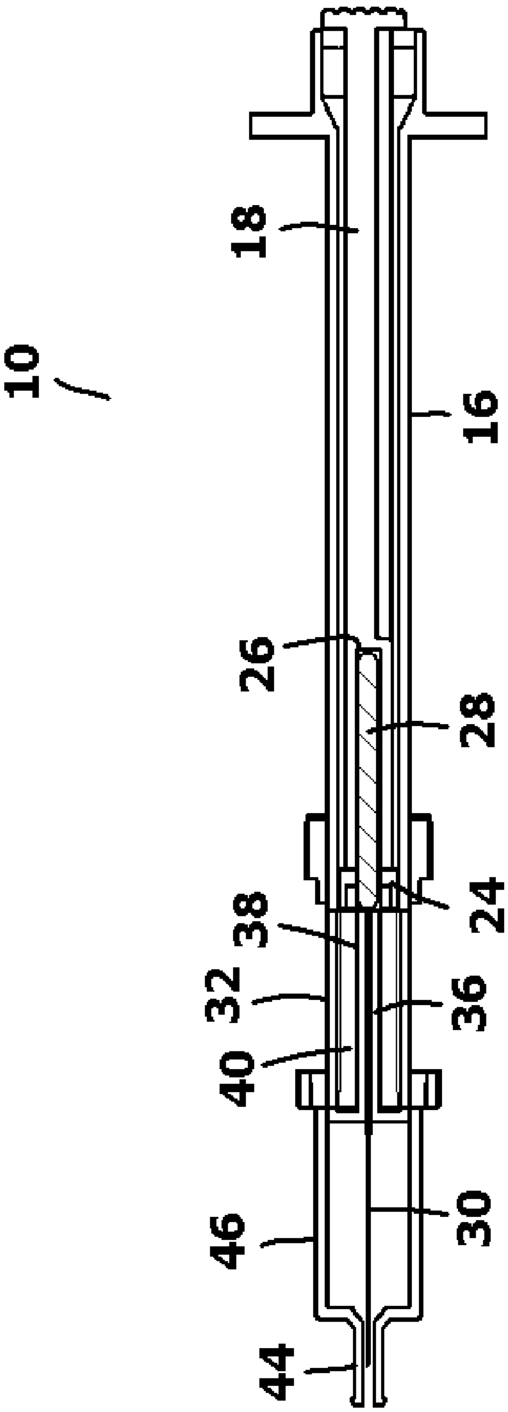
FIG. 7 shows a cross-section of the exemplary embodiment of FIG. 1 showing all material displaced from the needle and syringe system.

Referring to FIG. 6 and FIG. 7, it can be seen that after the needle and syringe assembly 10 is filled, the plunger rod 18 is manually advanced into the syringe barrel 16. The liquid previously drawn into the syringe barrel 16 is displaced through the needle 30. As the piston head 24 advances toward the head subassembly 12, the piston head 24 presses the tubular spacer 40 into the cylindrical cavity 38 around the central post 36 of the needle base 32. Simultaneously, the elongated plug 28 is pressed into the blind bore 26 in the plunger rod 18. As the piston head 24 contacts the central post 36, the tubular spacer 40 completely fills the cylindrical cavity 38. All liquid is displaced from the syringe barrel 16 except for the exceedingly small volume that remains inside the needle 30.

As the tubular spacer 40 is pressed forward by the advancing plunger rod 18, the tubular spacer 40 moves the actuator cap 46 forward relative the needle base 32. As the actuator cap 46 moves forward, the safety sheath 44 also moves forward, wherein the safety sheath 44 covers the tip of the needle 30. As a consequence, the needle 30 is shielded and rendered harmless just as the syringe barrel 16 empties.

It will be understood that the embodiment of the present invention that is illustrated and described is merely exemplary and that a person skilled in the art can make many variations to that embodiment. All such embodiments are intended to be included within the scope of the present invention as defined by the appended claims.

What is claimed is:

1. A needle and syringe system, comprising:
- a syringe barrel having an interior;
- a plunger rod having a first end and an opposite second end, said plunger rod having a bore formed therein that is accessible from said first end, wherein said bore extends for a first length into the plunger rod from said first end, and wherein said plunger rod can be reciprocally moved within said syringe barrel between a first position and a second position;
- a needle extending through a central post of a needle base;
- a tubular spacer that defines a central conduit, wherein said central post of said needle base and said central conduit of said tubular spacer have an equal length, wherein said first end of said plunger rod is closest to said tubular spacer when in said first position within said syringe barrel and is further from said tubular spacer when in said second position within said syringe barrel; and
- a plug having a length at least as long as said first length of said bore, said plug being separate and distinct from both said plunger rod and said tubular spacer, wherein said plug is initially disposed within said central conduit of said tubular spacer and leaves said central conduit to transfer into said bore on said plunger rod as said plunger rod is moved between said first position and said second position for a first time, wherein said plug completely blocks said central conduit of said tubular spacer and isolates said needle from said interior of said syringe barrel when said plug is present within said central conduit of said tubular spacer and wherein said plug completely fills said bore when fully received within said bore.

2. The system according to claim 1, wherein said bore is sized to receive all of said plug therein.

3. The system according to claim 1, further including a collar that selectively connects to said syringe barrel, wherein said collar supports said needle base that extends into said central opening of said tubular spacer.

4. The system according to claim 1, further including a safety sheath that surrounds part of said needle, and wherein said safety sheath can move relative to said needle to selectively shield said needle.

5. The system according to claim 4, wherein said plunger rod contacts and advances said tubular spacer as said plunger rod moves from said first position to said second position.

6. The system according to claim 5, wherein said needle base moves through said central opening in said tubular spacer as said tubular spacer is advanced by said plunger rod.

7. The system according to claim 5, wherein said plug is displaced out of said central opening of the tubular spacer and into said plunger rod as said plunger rod contacts and displaces said tubular spacer.

8. A needle and syringe system, comprising:
- a syringe assembly that contains a barrel and a plunger, wherein said barrel has an interior and wherein said plunger has an opening formed therein that is accessible from within said barrel, wherein said opening extends a first length into said plunger;
- a tubular spacer disposed in said barrel, said tubular spacer having a central opening extending therethrough;
- a needle head that selectively attaches to said syringe assembly, wherein said needle head has a needle that extends from a needle base, wherein said needle base extends into said central opening of said tubular spacer and wherein said needle base and said central opening of said tubular spacer have an equal length;
- a plug that is separate and distinct from both said plunger and said tubular spacer, said plug being initially positioned in said central opening of said tubular spacer, wherein said plug blocks said central opening and isolates said needle from said interior of said barrel, wherein said plug moves out of said central opening of said tubular spacer and moves into said opening in said plunger the first time said plunger moves to said tubular spacer in said barrel, and wherein said plug completely fills said opening in said plunger when received into said opening.

9. The system according to claim 8, wherein said opening in said plunger is sized to receive all of said plug therein.

10. The system according to claim 8, wherein said needle assembly further includes a safety sheath that surrounds part of said needle, and wherein said safety sheath can move relative to said needle.

11. The system according to claim 8, wherein said plunger contacts and advances said tubular spacer as said plunger moves toward said needle head within said barrel.

12. The system according to claim 11, wherein said needle base moves through said central opening in said tubular spacer as said tubular spacer is advanced by said plunger.

* * * * *